United States Patent [19]
Martinez et al.

[11] Patent Number: 4,944,757
[45] Date of Patent: Jul. 31, 1990

[54] MODULATOR KNEE PROSTHESIS SYSTEM

[76] Inventors: David M. Martinez, 5486 Quail Ridge, Camarilo, Calif. 93010; Roger G. Carignan, 2570 Calle Abedul, Thousand Oaks, Calif. 91360; S. David Stulberg, 5739 S. Blackstone Ave., Chicago, Ill. 60607

[21] Appl. No.: 268,056
[22] Filed: Nov. 7, 1988
[51] Int. Cl.⁵ ............................................... A61F 2/38
[52] U.S. Cl. ..................................................... 623/20
[58] Field of Search ................................. 623/16–23; 128/92 YP, 92 YL, 92 VW, 92 VL

[56] References Cited
U.S. PATENT DOCUMENTS 4,219,893  9/1980  Noiles ................................. 623/20
4,257,129  3/1981  Volz .
4,731,086  3/1988  Whiteside et al. .................. 623/20

FOREIGN PATENT DOCUMENTS 0010527  4/1980  European Pat. Off. ............. 623/20

OTHER PUBLICATIONS

Tibial Component Fixation In Deficient Tibial Bone Stock, P. Brooks et al., Clinical Orthopaedics and Related Research, vol. 184, Apr. 1984, pp. 302–308.

Primary Examiner—Richard J. Apley
Assistant Examiner—David F. Crosby
Attorney, Agent, or Firm—Cislo & Thomas

[57] ABSTRACT

A modular knee joint prosthesis using variably sized components for joining a variably resected tibia bone and a femur bone, having a tibial platform defining peripheral edges on its bottom surface for engaging beveled edges of the plates or spacers. The platform has an upraised boss on a top surface for engaging a tibial insert which can be locked in place with a lock key. The tibial insert serves as an articulating surface for a femoral component. An implantable stem extends below the platform and may be complementarily joined to a second stem; the stems lock together using a Morse taper and a locking bolt. Full-sized or half-sized extension plates have beveled edges on a top surface to engage complementing edges on the bottom surface of the tibial base plate. The plates act as a spacer or cap to the resected tibia and act to distribute load or make up for bone deficits.

20 Claims, 2 Drawing Sheets

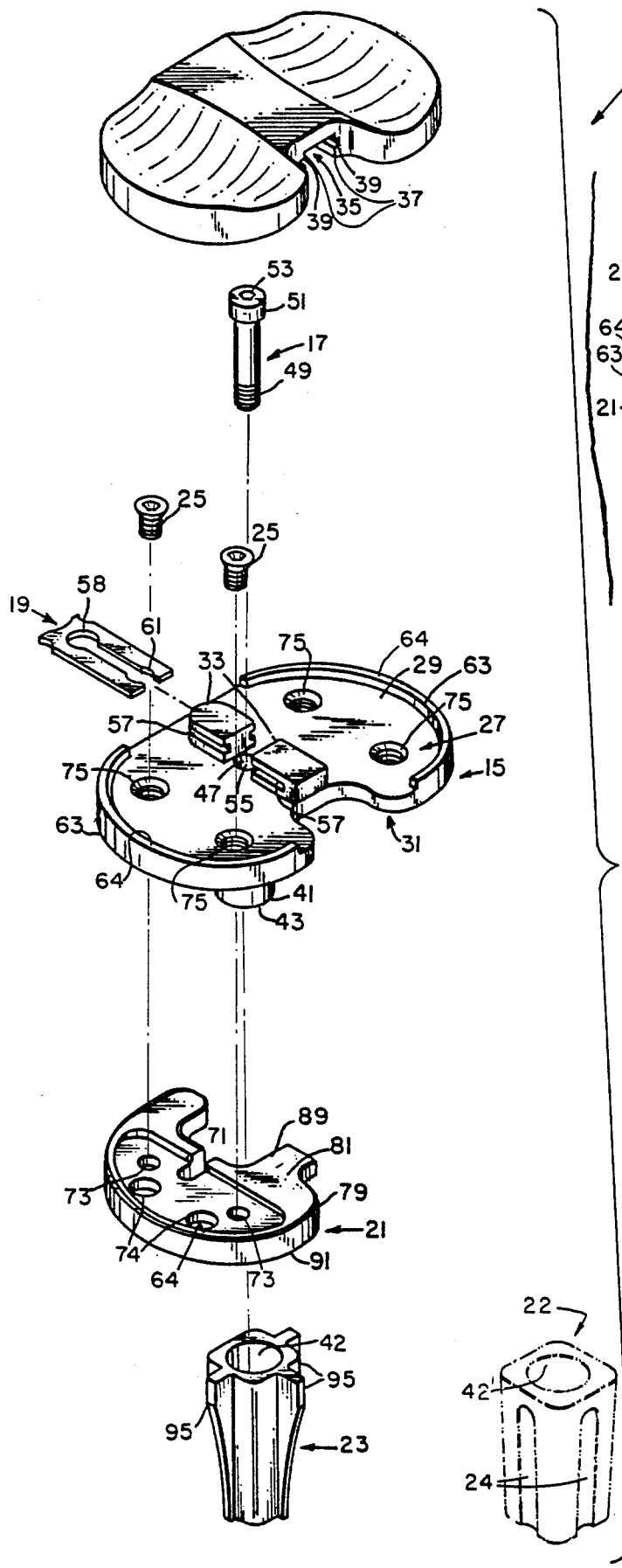
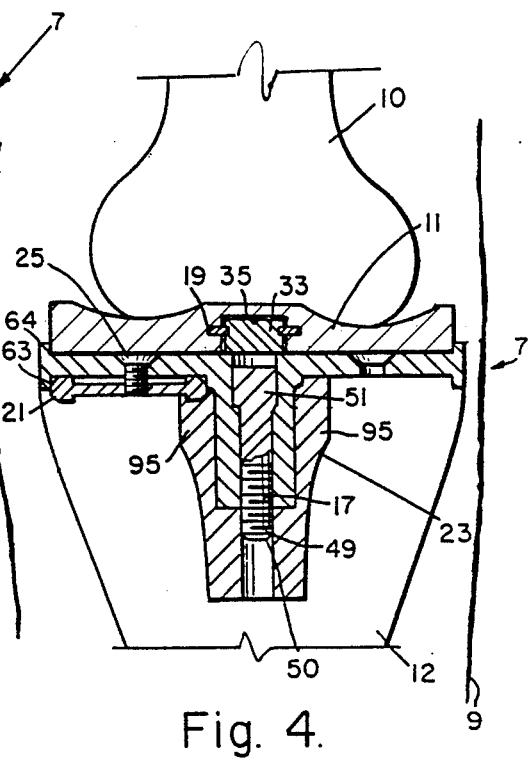
Fig. 2.
Fig. 4.

MODULATOR KNEE PROSTHESIS SYSTEM

This invention in general relates to prosthetic devices and implants such as artificial joints, and more particularly knee joints.

The knee joint is where the distal end of the femur and the proximal end of the tibia meet. Incorporated by reference herein are the background of the invention sections of the following U.S. Pat. No. 4,257,129 to Robert G. Volz and U.S. Pat. No. 4,714,474 to John G. Brookes, Jr. et al which disclose the particularities of the natural knee joint, problems associated with its replacement and discussions surrounding implantation of knee joint prostheses.

The main problem associated with knee joint implantation is that most prostheses restrict the surgeon to where resection of the tibia bone must take place. Furthermore, most prostheses do not allow for much adjustability to best accommodate the patient, thereby losing the ability to make a natural joint connection between the femur and the tibia.

The prosthetic device disclosed herein provides the greatest flexibility to the implanting surgeon offering the patient a prosthetic knee joint best simulating the natural knee joint. These results, as well as others, will be apparent from the hereinafter following commentary.

SUMMARY OF THE INVENTION

The present invention is directed to an improved knee joint prosthesis which offers a great degree of surgical flexibility at the time of implantation. The invention incorporates a modular system which allows the surgeon to structure and orient a knee prosthesis to best suit the patient.

More particularly, the knee joint prosthesis of the present invention allows the variable use of components to join a variably resected tibia bone to a femur bone. The system employs a tibial platform or base plate defining a top surface having an upraised boss. Along the periphery of the platform's bottom surface is an engaging and beveled lip. Extension plates of a variety of sizes may be placed under the tibial base plate. Also, a half-sized spacer may be used. The extension plates or half-sized spacers have beveled edges which engage the engaging and beveled lip assuring secure engagement.

A tibial insert providing an articulating surface for a femoral component engages the boss holding the tibial insert to the tibial base plate. A top surface of the base plate has a pair of engaging lips to prevent the tibial insert from sliding off the tibial platform. A lock key is used to lock the insert to the boss.

On the bottom side of the base plate is a concentrically narrowing stem which is axially located and which engages a modular stem which may have fins or anti-rotation grooves. The modular stem is implantable within the resected tibia bone. The engagement between the stem and modular stem utilizes a Morse taper fit on engagement. Also, a bolt may be incorporated through the stem for engagement to the modular stem.

Other aspects and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

FIG. 2 is an exploded perspective view of a knee joint prosthesis of the present invention with a modular half-spacer, and a modular stem is shown in phantom line;

FIG. 4 is a front side cross-sectional view taken along lines 4—4 of FIG. 3 of the knee joint prosthesis of the present invention.

DESCRIPTION OF THE PREFERRED EMBODIMENT

Figure 3:
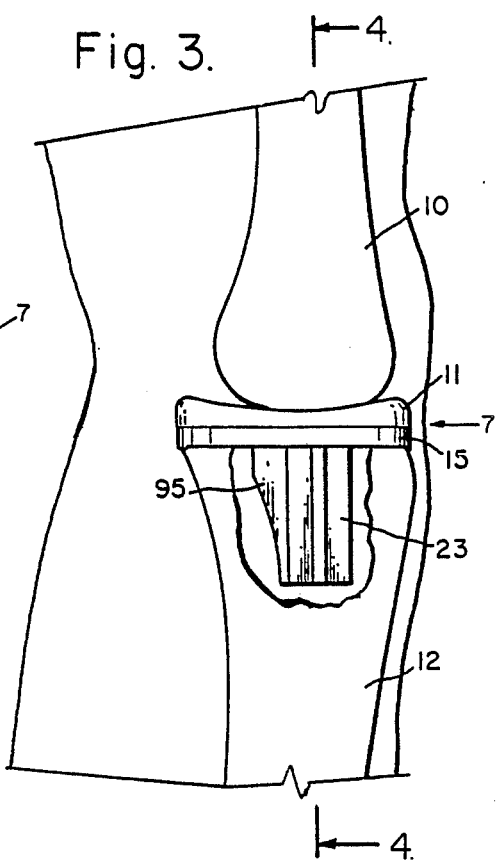
FIG. 3 is a right side cross-sectional view of the knee joint prosthesis of the present invention as shown in FIG. 2.

As shown in the drawings wherein like numerals identify like elements, the invention is embodied in a prosthetic knee joint 7. The joint 7 is implantable into a human leg 9, between the femur 10 and the tibia 12 bones. A femoral component 14 may be used to cap-off the distal end of the femur 10.

The joint 7 comprises a design and configuration which offers a great degree of modularity of components. The components comprise a tibial insert possibly a tibial extension plate 13 or modular half-spacer 21, a tibial platform or base plate 15, a stem bolt 17, a lock key 19, and a modular stem 22 or keel stem 23. Securing screws 25 may be utilized to secure the tibial extension plate 13 or the modular half spacer 21 to a bottom surface 31 of the tibial base plate 15. The screws 25 pass through the tibial base plate 15 to engage the extension plate 13 or modular half spacer 21.

A primary component is the tibial base plate or platform 15. The base plate or platform 15 has a kidney-shaped configuration having a top surface 29 and the bottom surface 31. An interrupted and upraised boss 33, primarily centered along the top surface 29 of the tibial base plate 15, is provided to operatively engage the tibial insert 11. A slot 35 along an undersurface of the tibial insert 11 is of a complementary shape and size to the boss 33. This allows a surgeon to easily slide the tibial insert 11 over the top surface 29 of the tibial base plate 15 to operatively engage the boss 33. The slot 35 has lateral and paralled grooves 39 on opposite and opposing walls 37. The engagement is snug and sufficient to prevent the insert 11 from sliding off the boss 33 or to cause shimming. Furthermore, the tibial base plate 15 has a pair of peripheral lips 64 on its top surface 29 which prevent anterior-posterior and medial-lateral movement of the tibial insert 11 upon assembly with the tibial base plate 15.

The lock key 19 has a circumferential shape and thickness adapted to slide into the grooves 39 of the slot 35. The lock key 19 has dual prongs of a type commonly known in the art of clips.

The tibial key 19 clips to the boss 33 in such a fashion, once the insert 11 is assembled upon the tibial base plate 15, so as to operatively and securely retain the insert 11 to the tibial base plate 15.

The tibial insert 11 can be selected from a large number of different ones varying in thickness, shape and design so long as the insert 11 has the requisite slot 35 and grooves 39 as described above.

Additionally, a standard or customized tibial extension plate 13 may be optionally positioned on the bottom surface 31 of the tibial base plate 15. The extension plate 13 may serve as both a spacer and a cap for the top of the resected tibia 12. The modular half-spacer 21, may be optionally placed on the bottom surface 31 instead of or in addition to the tibial extension plate 13 to act as on partial spacer, as shown in FIG. 2.

Extending downwardly from the bottom surface 31 of tibial base plate 15 is stem 41 centrally located and having a cylindrical and tapering end 43. The stem 41 engages a modular stem 22 shown in phantom line in FIGS. 1 and 2 or a keel stem 23 either of which may be implanted within the tibia 12 to be joined with the femur 10. The keel stem 2 has a receiving end 42 which is cylindrical and tapering inwardly to mate with the tapering end 43 of stem 41. When in an assembled condition, the stem 41 and keel stem 23 (or modular stem 23) form a Morse taper association to securely associate both stems 41 and 23. The keel stem 23 is often used in cementless surgical implanting techniques.

Figure 1:
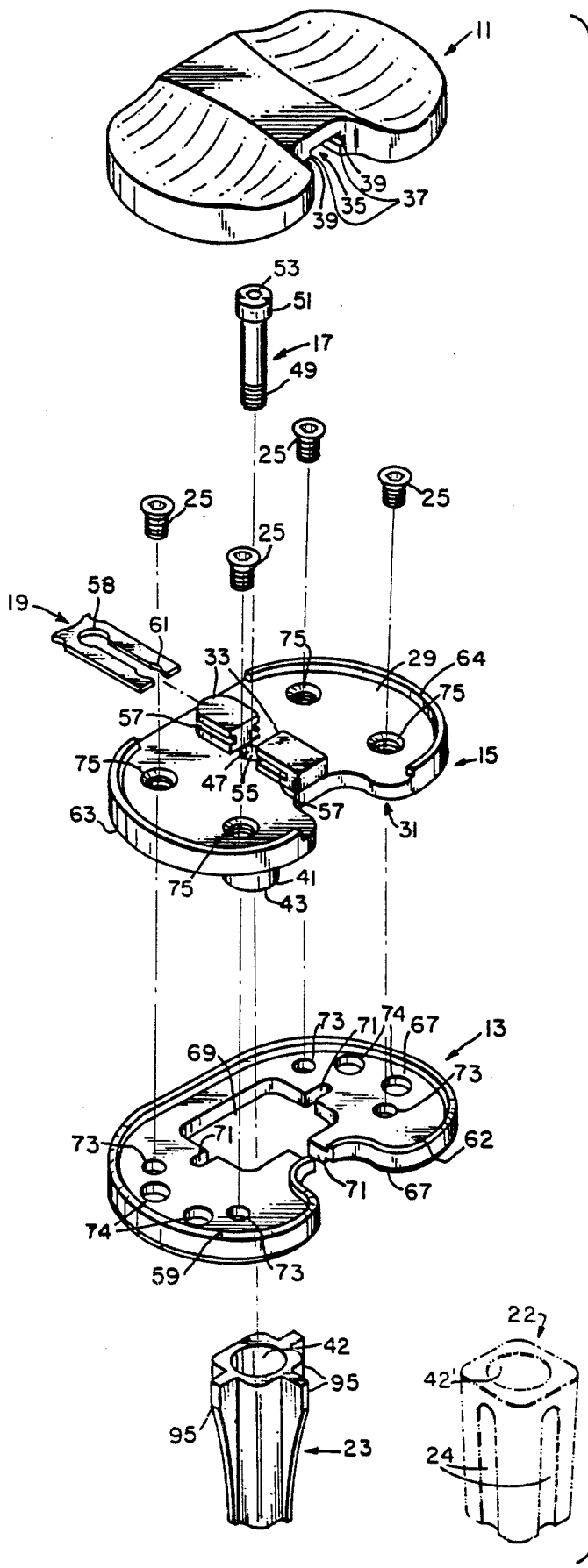
FIG. 1 is an exploded perspective view of a knee joint prosthesis of the present invention with an extension plate, and a modular stem is shown in phantom line.

Alternatively, stem 22 the modular stem 22 shown in phantom line in FIGS. 1 and 2, may have a clover-leaf cross-section with anti-rotation grooves 24 and a receiving end 42 and functions similar to the keel stem 23. The modular stem 22 is used in cementing surgical implanting techniques.

A bore 47 extends axially through the tibial base plate 15 and the stem 41 of the tibial base plate 15 and is of sufficient size to receive stem bolt 17. Stem bolt 17 has a threaded end 49 and an enlarged head 51 with a hexagonal recess 53 for engagement by a tool not shown. The bolt 17 passes through bore 47 and threadedly engages threads 50 within the interior of receptacle end 42 of keel stem 23 (or end 42 of the modular stem 22). The enlarged head 51 of bolt 17 is too large to pass through the bore 47 entirely, thereby securing the tibial base plate 15 to the keel stem 23 or modular stem 22.

The mid-section of the boss 33 is interrupted or discontinuous allowing a top opening 55 of the bore 47 to be exposed at a level flush with the top surface 29 of the tibial base plate 15. This allows the bolt 17 to be associated with the tibial base plate 15 and the keel stem 23 or modular stem 22 prior to the assembly of the tibial insert 11. Of course, as shown in FIG. 4, the bore 47 may be wider at its top opening 55 sufficient to allow the enlarged head 51 of the bolt 17 to fully recess into the bore 47, yet still retain the tibial base plate 15 to the keel stem 23 or the modular stem 22.

The boss 33, additionally, has corresponding grooves 57 positioned so as to allow the lock key 19 to slide into locking engagement with the boss 33 and the grooves 39 within the slot 35 of the tibial insert 11. Extending and curved surfaces on a bottom surface, not shown, of the boss's grooves 57 provide a locking feature, wherein the complementary curved surfaces 58 and 61 of the lock key 19 engage those surfaces on the boss 33 once the lock key 19 is slid into position.

The extension plate 13 or tibial base plate 15 may be asymmetrical or its periphery may be customized based upon a single cat scan (CT) slice of cross-sectional information so that the tibial base plate 15 or extension plate 13 fully covers the tibial bone 12. This configuration may achieve better loading on the proximal end of the tibial bone 12 to encourage proper healing. Customization may also take place using a variety of other imaging techniques to define the limits of the patient's bones. The image defined by the patient's, bones (primarily the proximal end of the tibia 12) dictates or defines the geometry of the extension plate 13 and/or the tibial base plate 15.

In more detailed aspects of the extension plate 13, the extension plate 13 has a kidney-shape configuration like the top surface 29 of the tibial base plate 15. However, the extension plate 13 may be slightly larger to act as an extending cover over the top of the resected tibia 12 in the event the tibial base plate 1 is not wide enough to satisfactorily cap off the end of the tibia 12. The extension plate 13 may range in thickness depending upon the patient encountered. Beveled edges 59 peripherally and uniformly circumscribed are located on a top surface 62 of the extension plate 13.

Although the extension plate 13 may come in a variety of sizes, the shape and size of the beveled edges 59 are uniform to allow modularity between different sized extension plates 13 and tibial base plates 15. The beveled edges 59 may have an inward inclination of 30° from lips 63 of the bottom surface 31 of the tibial base plate 15 in an assembled condition. The lips 63 may create a complementary angle or bevel from the horizontal or an angle so as to complement and engage the beveled edges 59 of the extension plate 13. The combination of lips 63 and edges 59 not only provides some degree of locking engagement, but also serves as a cement dam when cement is used to further secure the extension plate 13 to the bottom surface 31 of tibial base plate 15. The top surface 62 and a bottom surface 67 of the plate 13 may have an irregular surface for purposes of providing a better surface for engaging the component using cement.

The extension plate 13 defines a centrally located and rectangular cut-out section 69 with rounded corners which allows the extension plate 13 to be assembled on the bottom surface 31 of the tibial base plate 1 and allows the stem 41 to protrude through the extension plate 13.

The extension plate 13 may have positioning holes 74 uniformly positioned through the extension plate 13. Pegs or screws (not shown) can be positioned into the top of the tibia bone 12. The extension plate can be placed on the tibia bone 12 with the pegs or screws (not shown) passing through the holes 74 to position the extension plate 13. The tibial base plate 15 can then be positioned on the extension plate 13 to allow fastening of the tibial base plate 15 to the extension plate 13.

Additionally, slots 71 may interrupt the sides of the rectangular cut-out section 69 to accommodate the geometry or cross-section of the keel stem 23.

Also, screw holes 73 are evenly distributed across the extension plate 13 to allow the screws 25 to pas through the complementary spaced and sized holes 75 on the top surface 29 of the tibial base plate 15 and engage the extension plate 13 or half-spacer 21.

The half-spacer 21 is similar to the extension plate 13, but covers only half the area, has beveled edges 79 on a top surface 81 and engages lips 63 on the bottom surface 31 of the tibial base plate 15. A bottom surface 91 may have similar beveled edges for greater modularity. Screws 25 and cement may, likewise, secure the half-spacer 21 to one side of the bottom surface 31 or the other of the tibial base plate 15. The holes 75 in the tibial base plate 15 pass all the way through the tibial base plate so as to allow screw attachment via the top surface 29.

The modular half-spacer 21 may be optionally fastened to the tibial base plate 15 which allows the proper orientation of the tibial base plate 15, to the tibia 12, especially after a non-uniform or slanted resection of the tibia 12. The modular half-spacer 21 is attached to the tibial base plate 15 like the extension plate 13.

The half-spacer 21 may come in a variety of sizes, thicknesses, and angular cross-sections, however, its beveled edges 79 and holes 73 and 74 are uniformly positioned for modularity, fitting with a variety of different sized tibial base plates 15. Top and bottom surfaces 89 and 91 of the half-spacer 21 may also be irregular for cementing purposes. The half-spacer 21 allows the surgeon to buttress the tibial base plate 15 where the tibia bone 12 has not been resected perpendicularly to its longitudinal axis. This type of resection is often required where the proximal end of the tibia bone 12 has deteriorated due to disease or trauma or prior surgery.

Due to the modularity of the invention, the extension plate 13 could be positioned and attached to the bottom surface 31 of the tibial base plate 15 like the half-spacer 21.

The keel stem 23 or modular stem 22 can come in a variety of lengths, sizes and configuration. However, the receptacle ends 42 and 42 are of a uniform size as is the stem 41 of the tibial base plate 15 for purposes of interchangeability between components of different sizes. Also, threadings 50 shown within the interior of the receptacle end 42 of the keel stem 23 are of a uniform size to assure complete modularity.

In the preferred embodiment, the keel stem 23 is cylindrical with extending fins 95 which help stabilize the prosthesis 7 when implanted within the tibia bone 12. This stability helps prevent twisting disassociation of the prosthesis 7 from the tibia bone 12.

As mentioned, the tibial insert 11 is similar to those inserts as described by those tibial inserts described in the incorporated by reference patents, with the exception of the unique slot 35 and groove 39 configuration allowing for locking engagement with the boss 33 of the tibial base plate 15 using the lock key 19.

The materials used and their manufacture for each of the components are the same materials and methods of manufacture as those corresponding structures in the incorporated by reference patents, namely implantable cobalt chrome or titanium and ultra high molecular weight polyethylene plastic.

Implantation of the prosthesis 7 is similarly accomplished by the surgeon as current knee prostheses, however the surgeon has much greater flexibility in changing the overall fit, design, and attributes of the knee prosthesis once the implantation operation has started. After the surgeon has resected the tibia bone 12, he can quickly and easily build a prosthesis 7 to accommodate any situation he encounters. Also, the fit of the prosthesis can be enhanced with the variability of components and options that are available.

Furthermore, the present invention promotes greater bone surface to surface contact of the prosthesis. This contact distributes the stress of walking at the end of the joined bones, thereby acting to reduce resorption of the surrounding tissue away from the prosthesis.

In view of the foregoing, it should be appreciated that the present invention provides an improved modular knee joint prosthesis, which is simple in construction, completely modular and interchangeable, and superiorly effective.

Although the present invention has been described in detail with reference only to the presently-preferred embodiment, it will be appreciated by those of ordinary skill in the art that various modifications can be made without departing from the invention. Accordingly, the invention is limited only by the following claims.

We claim:

1. A modular knee joint prosthesis variably using selected prosthetic components to join a variably resected tibia bone to a femur bone comprising:
   a tibial platform defining a tibia implantable stem on a bottom surface and an upraised boss on a top surface which is adapted to engage a surface operatively associated with the femur, said platform having engaging and peripheral edges on a bottom surface of said platform to engage components to vary the orientation of said platform between and relative to said femur and tibia bones.

2. A modular knee joint prosthesis as claimed in claim 1, further comprising a tibial insert positioned over and engagable to said boss to provide an articulating surface between said surface of the femur bone and said platform.

3. A modular knee joint prosthesis as claimed in claim 2, wherein said upraised boss has a slotted end and wherein said tibial insert further defines a slot which allows said insert to slide over said boss to provide secure attachment thereto, said prosthesis further comprising a lock key which is slidably associated around said boss to engage said slotted end to retain said insert to said boss in an associated relationship.

4. A modular knee joint prosthesis as claimed in claim 3, wherein said stem is cylindrically tapered downwardly away from said platform, said prosthesis further defining a second stem having a receptacle end to complementarily receive and engage said stem of said tibial platform, and wherein said second stem is implantable in the tibia bone.

5. A module knee joint prosthesis as claimed in claim 4, further comprising a bolt, wherein said stem of said tibial platform defines a bore axially located and through said tibial platform and said second stem defines a corresponding aperture allowing said bolt to pass through said tibial platform and engage said aperture of said second stem, wherein said peripheral edges can engage bevelled edges of said components which may be secured to said bottom surface of said platform.

6. A module knee joint prosthesis as claimed in claim 1, further including a tibial extension plate of a predetermined size and having a top surface and a bottom surface, said top surface of said extension plate defining bevelled edges adapted to engage said edges of said bottom surface of said tibial platform when in an assembled condition.

7. A modular knee joint prosthesis as claimed in claim 6, wherein said extension plate has a geometry to allow a portion of said tibial platform to extend through said extension plate.

8. A modular knee joint prosthesis as claimed in claim 7, wherein said extension plate has a geometry compatible with the geometry of the tibia bone as determined by an electronic imaging technique.

9. A modular knee joint prosthesis as claimed in claim 8, wherein said tibial platform has a geometry compatible with the geometry of the tibia bone as determined by an electronic imaging technique.

10. A custom revision knee system which allows a surgeon to restore a patient's knee geometry and optimize fit, the system comprising:
   (a) a tibial base plate of a predetermined size having a top surface and a bottom surface, said bottom surface defining a bevelled lip, and said top surface defining an axially extending stem;

(b) a tibial extension plate of a predetermined size and having a top surface and a bottom surface, said top surface of said extension plate defining bevelled edges so as to engage said bevelled lip of said tibial base plate when in an assembled condition, said extension plate having a geometry to allow said extending stem of said tibial base plate to extend through said extension plate; and (c) a tibial insert of a predetermined size defining a top articulating surface and a bottom insert surface sized to be assembled upon said base plate, said tibial insert further defining a slot along said bottom insert surface allowing said insert to engage said upraised boss when in an assembled condition.

11. A custom revision knee system as claimed in claim 10, wherein said stem of said tibial base is concentrically tapered away from said bottom surface of said tibial base plate, and said system further comprising a second stem of a predetermined shape and size having a receptacle end axially located and complementarily shaped to said end of said stem of said tibial base plate for receiving said stem of said tibial base plate in engagement when in an assembled position.

12. A custom revision knee system as claimed in claim 11, wherein said stem of said tibial base plate defines an axial bore therethrough allowing communication between said top surface of said tibial base plate and one end of said stem of said tibial base plate, said system further comprising a stem bolt wherein said stem bolt passes through said bore to engage said tibial base plate to said second stem when in an assembled condition.

13. A custom revision knee system as claimed in claim 12, wherein said upraised boss defines grooves at a predetermined location and said system further comprising a lock key of a size and shape sufficient to engage said grooves when said slot of said tibial insert is engaged by said upraised boss as to lock said insert to said tibial base plate when in an assembled condition.

14. A modular knee joint prosthesis variably using selected prosthetic components to join a variably resected tibia bone to a femur bone comprising:

a tibial platform defining a tibia implantable stem on a bottom surface and an upraised boss on a top surface which is adapted to engage a surface operatively associated with the femur, said platform having engaging and peripheral edges on a bottom surface of said platform to engage components to vary the orientation of said platform between and relative to said femur and tibia bones;

a tibial insert positioned over and engageable to said boss to provide an articulating surface between said surface of the femur bone and said platform;

wherein said upraised boss has a slotted end and wherein said tibial insert further defines a slot which allows said insert to slide over said boss to provide secure attachment thereto, and wherein said prosthesis further comprises a lock key which is slidably associated around said boss to engage said slotted end to retain said insert to said boss in an associated relationship;

wherein said stem is cylindrically tapered downwardly away from said platform, said prosthesis further defining a second stem having a receptacle end to complementarily receive and engage said stem of said tibial platform, and wherein said second stem is implantable in the tibia bone; and further comprising a bolt, wherein said stem of said tibial platform defines a bore axially located and through said tibial platform and said second stem defines a corresponding aperture allowing said bolt to pass through said tibial platform and engage said aperture of said second stem.

15. A modular knee joint prosthesis as claimed in claim 14, further including a tibial extension plate of a predetermined size and having a top surface and a bottom surface, said top surface of said extension plate defining bevelled edges adapted to engage said edges of said bottom surface of said tibial platform when in an assembled condition.

16. A modular knee joint prosthesis as claimed in claim 15, wherein said extension plate has a geometry to allow a portion of said tibial platform to extend through said extension plate.

17. A modular knee joint prosthesis as claimed in claim 16, wherein said extension plate has a geometry compatible with the geometry of the tibia bone as determined by an electronic imaging technique.

18. A modular knee joint prosthesis as claimed in claim 17, wherein said tibial platform has a geometry compatible with the geometry of the tibial bone as determined by an electronic imaging technique.

19. A custom revision knee system which allows a surgeon to restore a patient's knee geometry and optimize fit, the system comprising:

a tibial base plate of a predetermined size having a top surface and a bottom surface, said bottom surface defining a bevelled lip and an axially extending stem, and said top surface defining an upraised boss;

a tibial extension plate of a predetermined size having a top surface and a bottom surface, said top surface of said extension plate defining bevelled edges so as to engage said bevelled lip of said tibial base plate when in an assembled condition, said extension plate having a geometry to allow said extending stem of said tibial base plate to extend through said extension plate;

a tibial insert of a predetermined size defining a top articulating surface and a bottom insert surface sized to be assembled upon said base plate, said tibial insert further defining a slot along said bottom insert surface allowing said insert to engage said upraised boss when in an assembled condition;

wherein said stem of said tibial base is concentrically tapered away from said bottom surface of said tibial base plate, and said system further includes a second stem of a predetermined shape and size having a receptacle end axially located and complementarily shaped to said end of said stem of said tibial base plate for receiving said stem of said tibial base plate in engagement when in an assembled condition; and wherein said stem of said tibial base plate defines an axial bore therethrough allowing communication between said top surface of said tibial base plate and one end of said stem of said tibial base plate, said system further comprising a stem bolt wherein said stem bolt passes through said bore to engage said tibial base plate to said second stem when in an assembled condition.

20. The custom revision knee system as claimed in claim 19, wherein said upraised boss defines grooves at a predetermined location and said system further comprises a lock key of a size and shape sufficient to engage said grooves when said slot of said tibial insert is engaged by said upraised boss as to lock said insert to said tibial base plate when in an assembled condition.

* * * * *